US005557201A

United States Patent [19]
Kleinberg et al.

[11] Patent Number: 5,557,201
[45] Date of Patent: Sep. 17, 1996

[54] PULSED NUCLEAR MAGNETISM TOOL FOR FORMATION EVALUATION WHILE DRILLING

[75] Inventors: Robert L. Kleinberg, Ridgefield; Abdurrahman Sezginer, Brookfield, both of Conn.

[73] Assignee: Schlumberger Technology Corporation, New York, N.Y.

[21] Appl. No.: 430,697

[22] Filed: Apr. 28, 1995

Related U.S. Application Data

[63] Continuation of Ser. No. 200,815, Feb. 22, 1994, abandoned, which is a continuation of Ser. No. 922,254, Jul. 30, 1992, abandoned.

[51] Int. Cl.$^6$ .................................................. G01R 33/20
[52] U.S. Cl. ............................................................. 324/303
[58] Field of Search ...................................... 324/300, 303, 324/318

[56] References Cited

U.S. PATENT DOCUMENTS

| | | | |
|---|---|---|---|
| Re. 32,913 | 4/1989 | Clark | 324/338 |
| 1,158,959 | 11/1915 | Beach | 494/27 |
| 3,205,477 | 9/1965 | Kalbfell | 73/151 |
| 3,360,716 | 12/1967 | Bloom et al. | 324/303 |
| 3,395,337 | 7/1968 | Varian | 324/303 |
| 3,402,344 | 9/1968 | Brown et al. | 324/303 |
| 3,617,867 | 11/1971 | Herzog | 324/303 |
| 3,667,035 | 5/1972 | Slichter | 324/303 |
| 3,777,560 | 12/1973 | Guignard | 73/151.5 |
| 3,784,898 | 1/1974 | Darley et al. | 324/303 |
| 4,350,955 | 9/1982 | Jackson et al. | 324/303 |
| 4,479,564 | 10/1984 | Tanguy | 181/105 |
| 4,536,714 | 8/1985 | Clark | 324/338 |
| 4,629,986 | 12/1986 | Clow et al. | 324/303 |
| 4,656,422 | 4/1987 | Vail, III et al. | 324/303 |
| 4,710,713 | 12/1987 | Strikman | 324/303 |
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,785,245 | 11/1988 | Lew et al. | 324/308 |
| 4,792,757 | 12/1988 | Vail, III et al. | 324/303 |
| 4,825,163 | 4/1989 | Yabusaki et al. | 324/318 |
| 4,829,252 | 5/1989 | Kaufman | 324/309 |
| 4,875,013 | 10/1989 | Murakami et al. | 324/318 |
| 4,899,112 | 2/1990 | Clark et al. | 324/338 |
| 4,933,638 | 6/1990 | Kenyon et al. | 324/303 |
| 4,949,045 | 8/1990 | Clark et al. | 324/338 |
| 4,987,368 | 1/1991 | Vinegar | 324/303 |
| 5,023,551 | 6/1991 | Kleinberg et al. | 324/303 |
| 5,055,787 | 10/1991 | Kleinberg | 324/303 |
| 5,055,788 | 10/1991 | Kleinberg et al. | 324/303 |
| 5,138,263 | 8/1992 | Towle | 324/338 |
| 5,200,699 | 4/1993 | Baldwin et al. | 324/303 |
| 5,280,243 | 1/1994 | Miller et al. | 324/303 |
| 5,376,884 | 12/1994 | Sezginer | 324/303 |

FOREIGN PATENT DOCUMENTS

| | | | |
|---|---|---|---|
| 0295134 | 12/1988 | European Pat. Off. | G01V 3/32 |
| 2056082 | 3/1981 | United Kingdom | G01N 24/08 |
| 92/10768 | 6/1992 | WIPO | 324/303 |

OTHER PUBLICATIONS

Timur, A.; "Pulsed Nuclear Magnetic Resonance Studies of Porosity, Movable Fluid, and Permeability of Sand Stones", SPE–AIME, 1969, J. of Petroleum Technology.

Miller, M., et al; "Spin Echo Magnetic Resonance Logging: Porosity and Free Fluid Index Determination", SPE 20561. (1990).

Herrick, R., et al; "An Improved Nuclear Magnetic Logging System and its Application to Formation Evaluation", SPE 8361 (1979).

Jackson, J., et al. "Remote (Inside–Out) NMR III. Detection of NMR in a Remotely Produced Region of Homogenous Magnetic Field," Academic Press May, 1980.

Primary Examiner—Sandra L. O'Shea
Assistant Examiner—Raymond Y. Mah
Attorney, Agent, or Firm—Leonard W. Pojunas

[57] ABSTRACT

The instruments of a pulsed nuclear magnetic resonance (NMR) device are included in a drill collar for evaluating earth formations. The resulting tool makes NMR measurements while the formation is being drilled.

44 Claims, 5 Drawing Sheets

PULSED NUCLEAR MAGNETISM TOOL FOR FORMATION EVALUATION WHILE DRILLING

This is a file wrapper continuation of Ser. No. 08/200,815, filed Feb. 22, 1994, abandoned, which is a file wrapper continuation of parent application Ser. No. 07/922,254, filed Jul. 30, 1992, abandoned.

FIELD OF THE INVENTION

The invention concerns a tool for logging while drilling. More specifically the invention concerns a tool for logging a formation using pulsed nuclear magnetic resonance (NMR) techniques while drilling a borehole into the formation.

BACKGROUND OF THE INVENTION

Several pulsed NMR tools have been designed for borehole deployment via wireline and are described in U.S. Pat. Nos.:

4,350,955, issued September 1982 to Jackson et al.;

4,629,986, issued December 1986 to Clow et al.;

4,710,713, issued December 1987 to Strikman;

4,717,876, issued January 1988 to Masi et al.;

4,717,877, issued January 1988 to Taicher et al.;

4,717,878, issued January 1988 to Taicher et al.;

4,714,881, issued December 1987 to Givens;

5,023,551, issued June 1991 to Kleinberg et al.;

5,055,787, issued October 1991 to Kleinberg et al.; and 5,055,788, issued October 1991 to Kleinberg et al.

All of these patents describe NMR tools which employ permanent magnets to polarize hydrogen nuclei, and RF coils to excite and detect nuclear magnetic resonance to determine porosity, free fluid ratio, or permeability of a formation, for example. The tools described in U.S. Pat. Nos. 4,717,877; 5,055,787; and 5,055,788 have been successfully tested in boreholes.

The instrument concepts described in the related patents U.S. Pat. Nos. 4,710,713 and 4,717,877 have a rotationally invariant region of resonance, which is a thin cylindrical shell coaxial with the borehole. The electromagnetic fields have a simple azimuthal dependence: both the static and RF fields at any point in the vicinity of the instrument rotate at the same rate as the instrument rotates. The rotation does not disturb the NMR measurement because the nuclear magnetic moment adiabatically tracks the magnetic field. The radial thickness of the resonance region of these instruments is on the order of 1 mm.

The instrument concepts described in the related patents U.S. Pat. Nos. 4,350,955, 4,629,986, and 4,717,876 have rotationally invariant static and RF fields and a relatively large resonant region (at least 10 mm thick). The resonant region is thicker because the magnitude of the magnetic field is stationary at the resonant region. These patents, however, do not describe rotating the instruments.

Several logging while drilling (LWD) and measuring while drilling (MWD) tools have been designed for formation evaluation while drilling and drill string characterization while drilling, respectively. Logging or measuring instruments are placed in drill collars up to 100 ft behind the drill bit. An MWD tool is described in U.S. Pat. Nos. 3,777,560 to Guignard and 4,479,564 to Tanguy. An LWD tool is described in U.S. Pat. Nos. 4,899,112 to Clark et al. and 4,949,045 to Clark et al. Typically, these tools use electromagnetic techniques in evaluating resistivity of a formation while drilling.

None of the NMR tools have been used in a drilling string, nor have the LWD or MWD tools used pulsed NMR techniques.

SUMMARY OF THE INVENTION

The invention concerns an apparatus comprising a drilling means for drilling a borehole in an earth formation; and a measuring means, connected to the drilling means, for making nuclear magnetic resonance (NMR) measurements while the borehole is being drilled.

In a preferred embodiment, the invention concerns a drill string and bit for drilling a borehole in an earth formation and a pulsed NMR device which is housed by the drill swing. The embodiment includes a channel within the drill string and pulsed NMR device through which drilling mud is pumped into the borehole. The pulsed NMR device comprises two tubular magnets which are mounted within the drill swing to surround the channel. The pulsed NMR device also includes an antenna coil mounted in a recess in the exterior surface of the drill string and between the two tubular magnets, and associated driving circuitry located in a compartment of the drill string. Thus, the tool logs the earth formation using pulsed NMR techniques while the tool drills a borehole into the formation.

DETAILED DESCRIPTION

Because the resonance region of the instruments of U.S. Pat. Nos. 4,710,713 and 4,717,877 is on the order of 1 mm, the inventors expect that lateral vibrations of a drill collar which might be proposed for containing an NMR device would adversely affect an NMR measurement. For example, a lateral, 50 Hz vibration of 1 mm amplitude (10 g acceleration) would disable the measurement. Also, the inventors have determined that, since the drill string makes several revolutions in the duration of a pulsed NMR measurement (on the order of 1 second), an NMR instrument in a drilling string must be rotationally symmetric. Accordingly, the instrument of this invention provides greater immunity to lateral motion and is also rotationally symmetric about a longitudinal axis. A detailed description of the tool follows.

Figure 1:
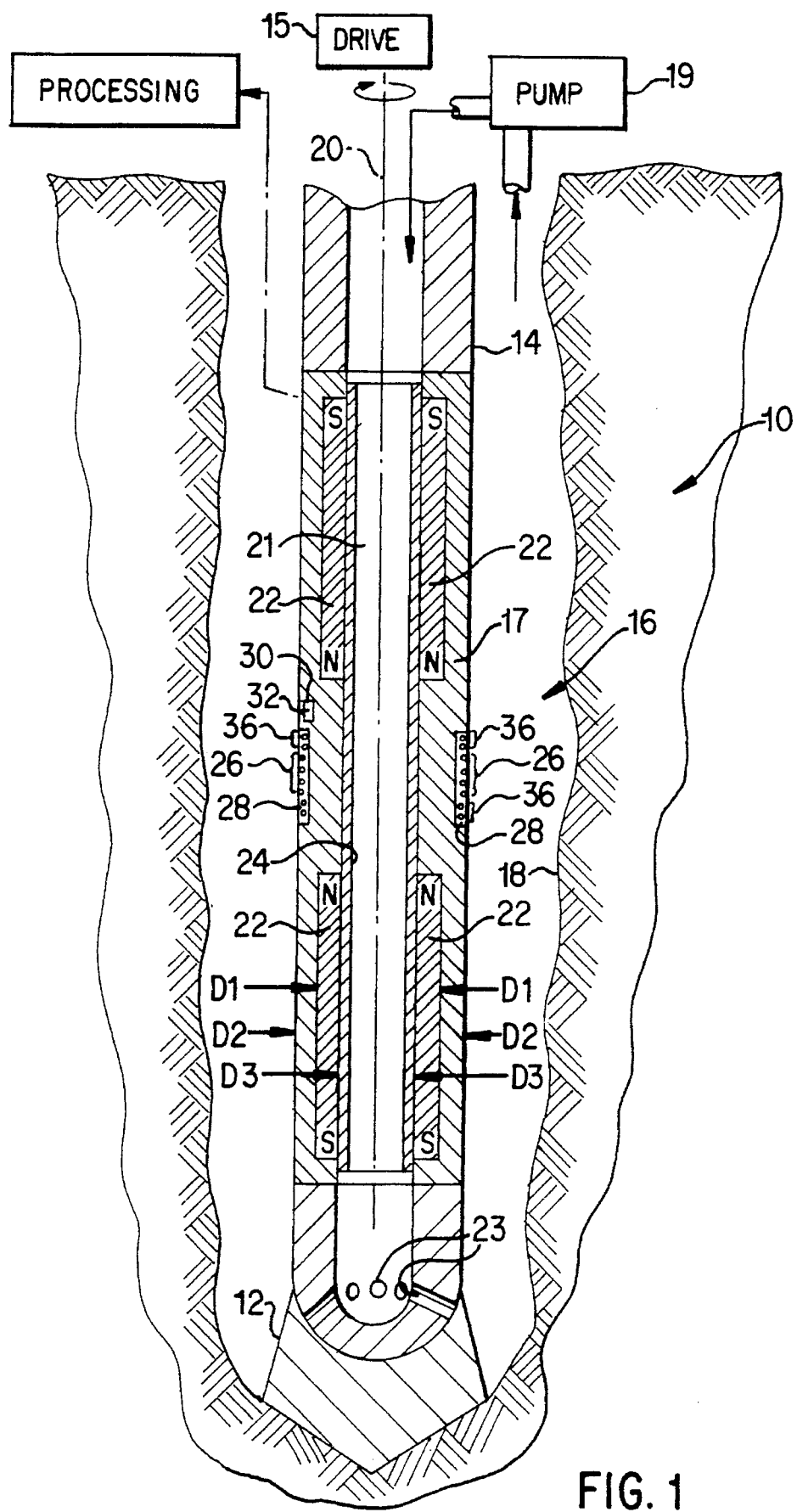
FIGS. 1 and 3A show a cross section of a tool for pulsed NMR formation evaluation while drilling.

FIG. 1 shows a tool 10 according to this invention. The tool 10 includes a drill bit 12, drill string 14, and pulsed NMR device 16 (housed within a drill collar 17). The drill bit 12 and drill string 14 comprise a means for drilling a borehole 18 in an earth formation. A drive mechanism 15 rotates the drill string 14 and drill bit 12 as is known in the art. See U.S. Pat. No. 4,949,045 to Clark et al., for example. The drill collar 17 is made of a nonmagnetic alloy. The tool 10 also comprises a means for making pulsed nuclear magnetic resonance (NMR) measurements while a borehole 18 is being drilled. The pulsed NMR device 16 is connected as part of the drill string 14 and is housed within the drill string 14. As seen in FIG. 1, the pulsed NMR device 16 is rotationally symmetric about a longitudinal axis 20 of the drill string 14.

The borehole 18 typically contains fluid, such as drilling muds which are pumped by pump 19 into the borehole 18 from the surface to carry away formation cuttings back to the surface. Such a pump is described in U.S. Pat. No. 4,949,045 to Clark et al., for example. A channel 21 within the drill swing 14 comprises a means for carrying the borehole fluid through the drill string 14. The channel 21 is cut within the drill collar 17 substantially parallel to the longitudinal axis 20. The channel 21 opens to the borehole 18 through ports 23 in the drill bit 12.

Figure 2:
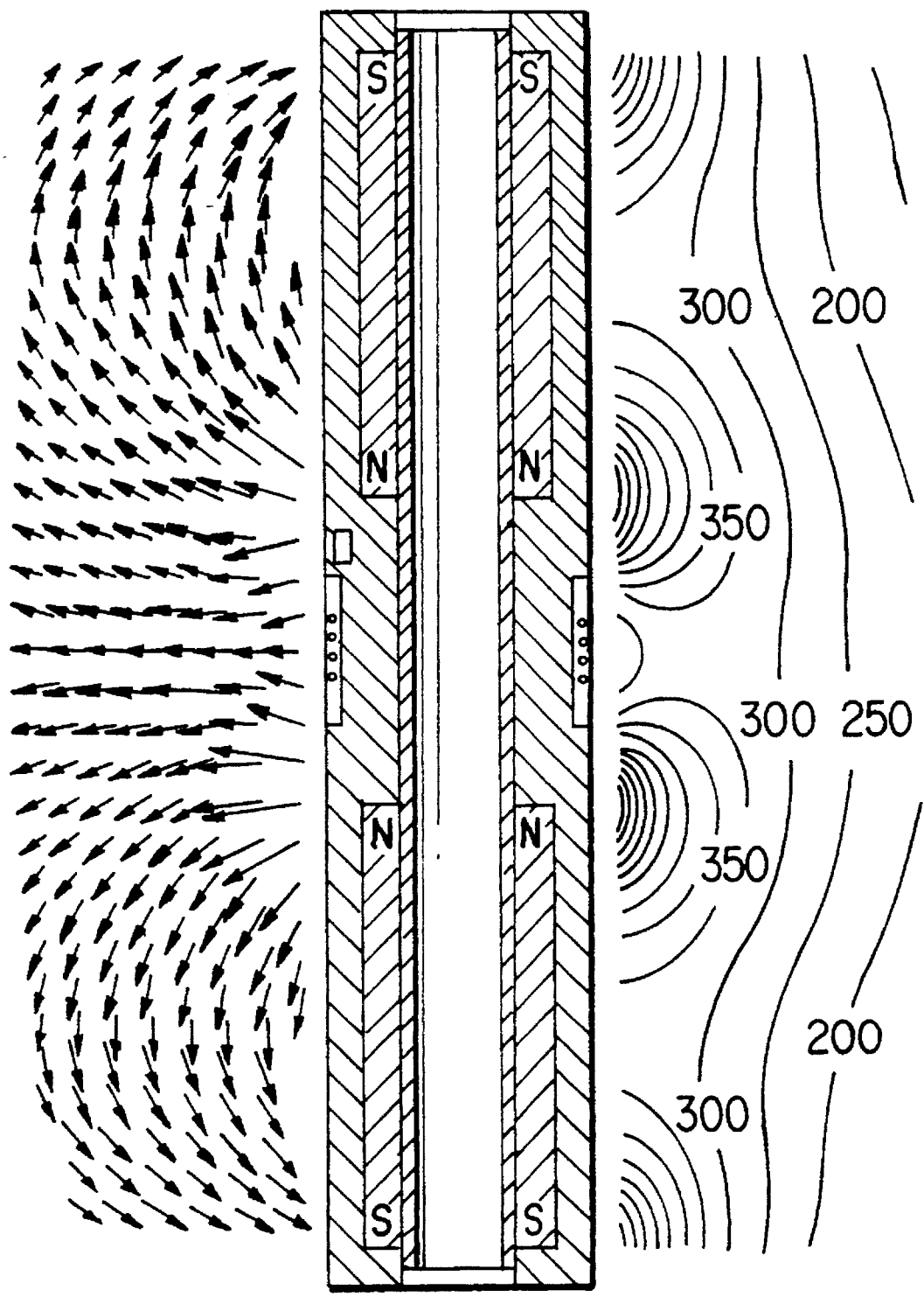
FIG. 2 shows a static field in a vertical plane of the tool of FIG. 1.
Figure 3:
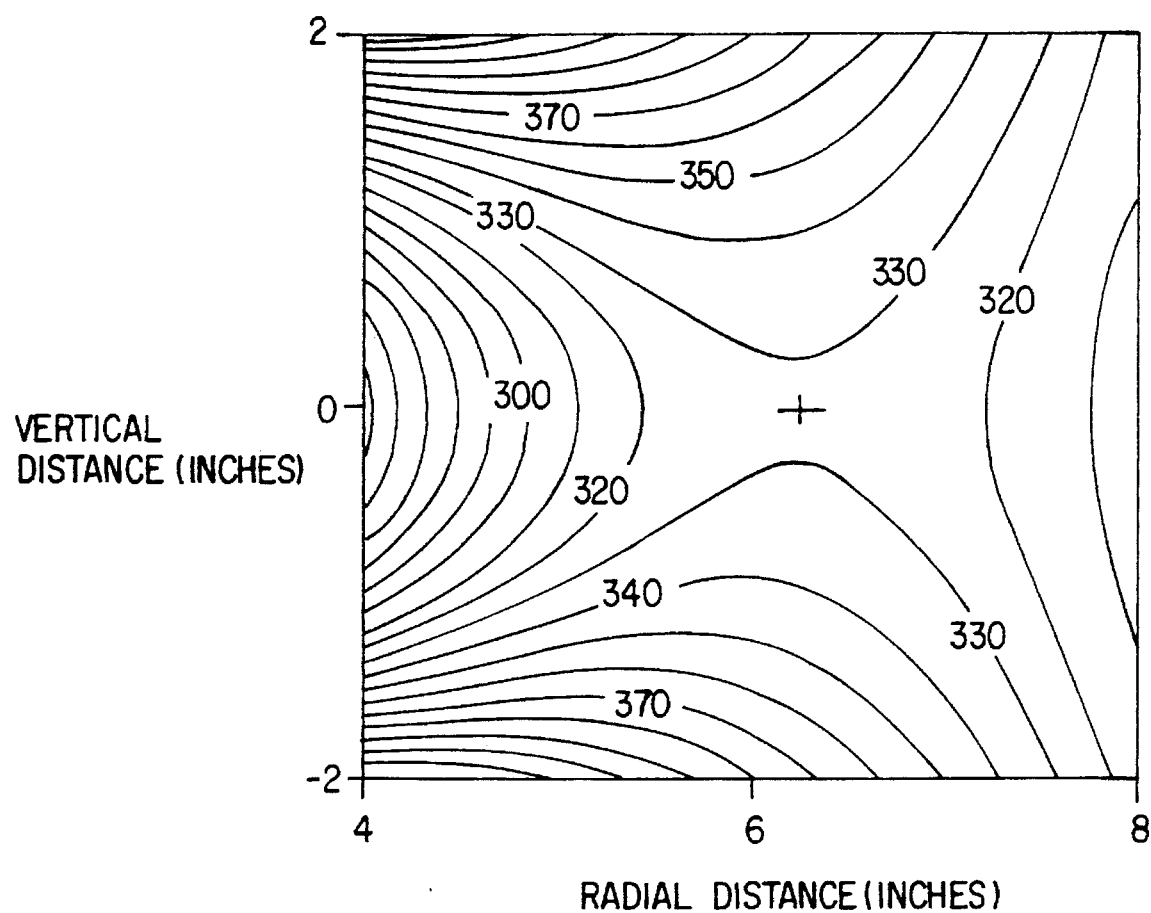
FIG. 3 shows a static magnetic field of the tool of FIG. 1.

The pulsed NMR device 16 comprises, in a preferred embodiment, a pair of tubular magnets 22 arranged and housed in the drill string 14 and within the pulsed NMR device 16 to surround the channel. The two sleeve shaped, tubular magnets 22 are permanently magnetized in the axial direction and are positioned in opposing directions. In FIGS. 1–3 the north magnetic poles of the two tubular magnets 22 face one another, for example. The magnets 22 are preferably made of Samarium-Cobalt, which has a high remanence, coercive force, and Curie temperature. The magnets 22 can be installed into a recess that is cut out either from the outside or from the inside of the drill collar 17. Cutting from the inside is preferred because the bending and torsional strengths of the drill collar 17 are proportional to the difference of the fourth powers of the drill collar's outer and inner radii. For example, in FIG. 1 the inner D1 and outer D2 diameters of the drill collar 17 at the magnet-recess are 5.000" and 6.750", respectively. The inner D3 and outer D2 diameters of the magnets 22 are 3.000" and 5.000", respectively. These dimensional values, and those below, are only cited as examples. Numerous other values of the diameters, thickness, and depth are possible.

The magnets 22 are protected from the pressure and abrasion of drilling mud by a 0.375" thick nonmagnetic steel barrel 24, for example. The barrel 24 defines the channel 21 and is positioned to isolate the tubular magnets 22 from the drilling mud comprising the borehole fluid. Had the recess for the magnets 22 been made from outside surface of the drilling collar 17, the recess would have to be at most 0.276" deep, for example, in order to achieve the same mechanical strength. This shallow recess must be considered in accommodating the magnets 22 and the protective barrel 24. The inventors have found it is preferable to cut the recess for the magnets 22 from the inside of the drill collar 17 to obtain greater mechanical strength and sufficient space to accommodate the magnets 22 and steel barrel 24.

FIG. 1 also shows an RF antenna 26 located in an antenna recess 28 between the two tubular magnets 22. The pulsed NMR portion 16 of this tool 10 comprises the antenna 26 mounted on the drill collar 17 and the two tubular magnets 22. The antenna 26 is mounted in an exterior recess 28 of an exterior surface of the drill collar 17. The antenna recess 28 is preferably on the outside of the drill collar 17, because at the frequency of operation (around 1.4 MHz in the example in FIG. 1) the resulting RF magnetic field could not diffuse out through the drill collar 17.

Figure 3A:
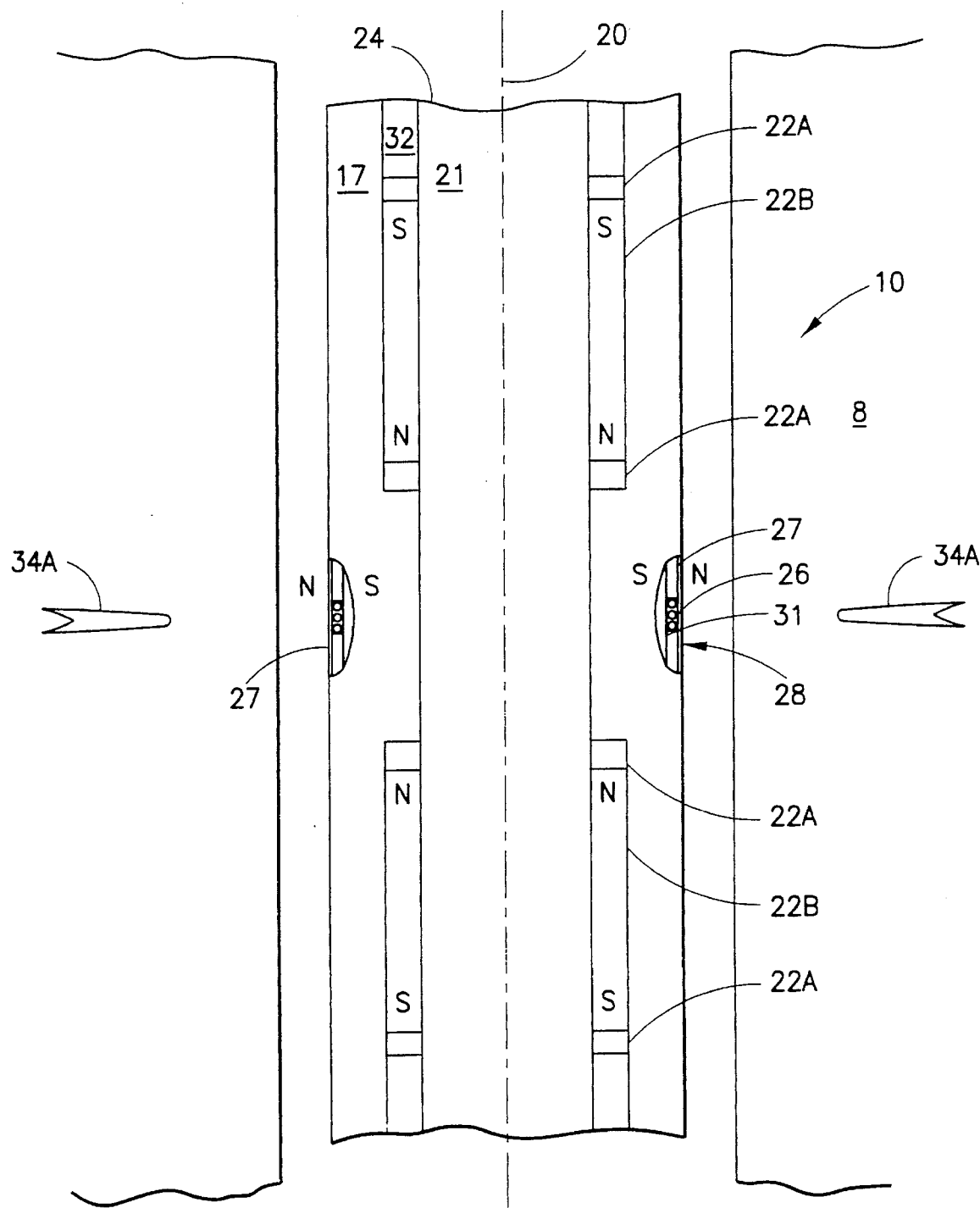

The antenna 26 preferably comprises a coil which also surrounds the channel. The antenna recess 28 is preferably filled with a nonconducting material such as plastic or rubber. Alternatively, the antenna recess 28 can also be filled with a ferrite to improve the efficiency of the RF antenna 26. The RF antenna 26 can be protected by a sheet-metal shield 27 with axial slots to let out the RF magnetic field. The slotted shield 27 is mounted in the recess 28 and radially outside the antenna 26 coil. See FIG. 3A Examples of the construction of the antenna and the slotted shield have been described in the U.S. Pat. No. 4,949,045 to Clark et al. issued August 1990 in the context of a Compensated Dual Resistivity Tool (mark of Schlumberger Technology Corporation), and U.S. Pat. No. 4,536,714 to Clark issued August 1985.

The pulsed NMR portion 16 of this tool 10 also includes driving circuitry. The drill collar 17 includes a compartment 30 in which the driving circuitry 32 is located. The small, atmospheric-pressure compartment 30 close to the RF antenna 26 houses the electronic, driving circuitry such as the Q-switch, duplexer, and preamplifier which drive the antenna and which have to be in close proximity of the RF antenna 26. This driving circuitry 32 is similar to that disclosed in the two U.S. Pat. Nos. to Kleinberg et al., 5,055,787 and 5,055,788.

The NMR device 16 is pulsed and the formation is logged according to the technique described in U.S. Pat. Nos. 5,055,787; 5,055,788; and 5,023,551 to Kleinberg et al. The information representing the evaluation of the formation is stored in a downhole memory (not shown) and is obtained from the pulsed NMR device 16 in a manner as described in U.S. Pat. No. 4,949,045 to Clark et al.

In FIG. 2, a static magnetic field provided by the pulsed NMR device 16 is shown in a vertical plane that contains the borehole axis (not shown). To the fight of the cross-section of the tool 10, the magnitude of the static field is illustrated by a contour map of 50 Gauss increments. The field is azimuthally symmetric. The pulsed NMR device 16 produces a field having a stationary point or saddle point, indicated by a (+) sign, in the formation. At this point, all spatial derivatives of the static magnetic field are zero. To the left of the cross-section of the tool 10, the magnitude and direction of the static field are illustrated by vectors.

FIG. 3 shows a resonance region 34 of the static magnetic field of FIG. 2 in greater detail using a contour map of 10 Gauss increments. The pulsed NMR device 16 produces the static magnetic field having the resonance region 34 which extends from the tool 10 into the formation under evaluation. In this example of the invention, the stationary point of the resonance region 34 is 6.25" away from the borehole axis (not shown). If the drill bit 12 size is 8.5" (diameter), then the stationary point is 2.00" away from the surface of the borehole 18 wall. According to this invention, the static magnetic field is produced such that the stationary point occurs in the formation. In this manner, a large resonance region 34 is produced making the pulsed NMR device 16 relatively immune to tool motions.

Figure 4:
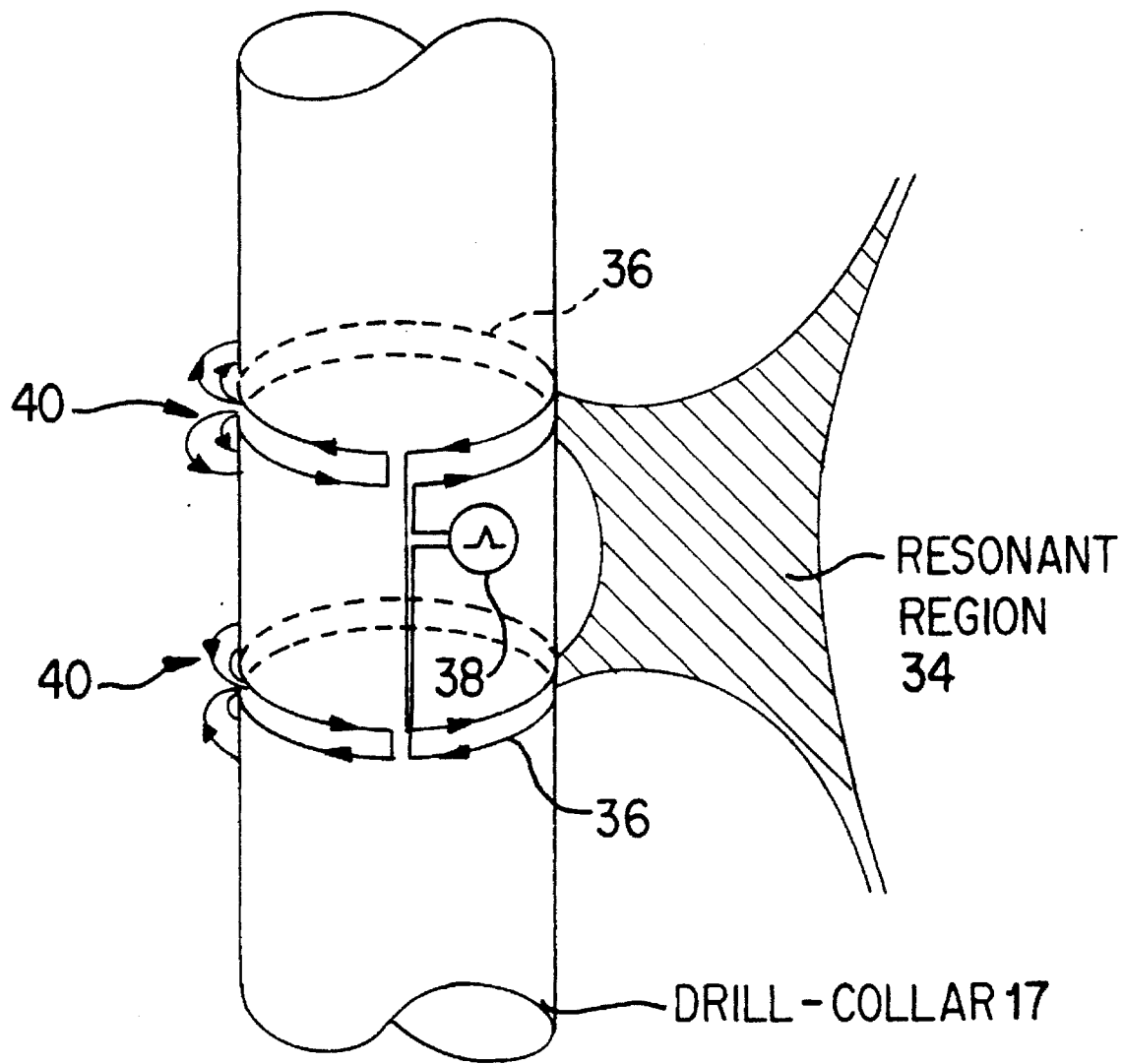
FIG. 4 shows a gradient coil according to the invention of FIGS. 1–3.

FIG. 4 shows the resonance region 34 extending into the borehole 18. Because the resonance region 34 extends into the borehole 18, an electromagnetic signal is produced in the borehole fluid. The resulting electromagnetic signal of the borehole fluid must be cancelled because the pulsed NMR device 16 functions by detecting protons in fluids. Typically, the rock formation is 10% fluid by volume, but the borehole fluid contains more than 50% fluid and has a high density of protons. For this reason, the electromagnetic signal of the borehole fluid would dominate any formation signal detected by the pulsed NMR device 16. The electromagnetic signal of the borehole fluid can be cancelled by applying a pulsed magnetic field that is strong in the borehole 18 but weak at the stationary point (+) of the static magnetic field. Such a field for cancelling the electromagnetic signal of the borehole fluid can be produced by a gradient-coil 36. A pulsed current source 38 drives the gradient-coil 36, which produces magnetic field lines 40. FIG. 4 shows the gradient-coil 36 is coiled around the longitudinal axis 20 of the drill collar 17, and, thus, around the pulsed NMR device 16. The gradient-coil 36 is coiled above and below the antenna 26, as viewed in FIG. 1. The gradient-coil 36 may be placed in the antenna recess 28, or in a separate recess in the drill collar 17. Most importantly, the gradient-coil 36 is sited to most effectively eliminate the signal from the borehole, such as in the vicinity of the extensions 42 of the resonance region 34. In this manner, the magnetic field lines 40 of the gradient-coil 36 cancel the electromagnetic signal of the borehole fluid in the vicinity of the extensions 42. The location of the extensions 42 of the resonance region 34 is a function of the material, size, shape, and spacing of the permanent tubular magnets 22. The gradient-coil 36 may be unnecessary when the drill string 14 is in motion. Since the part of the resonant region in the borehole 18 is a thin shell, vertical and lateral vibrations may eliminate the borehole signal.

We claim:

1. An apparatus comprising:
   1) a drilling means having:
      a) a drill bit for drilling a borehole in a formation;
      b) an exterior surface and a recess in the exterior surface; and
      c) a housing means;
   2) a pulsed NMR means housed within the housing means for making nuclear magnetic resonance (NMR) measurements of the formation while the borehole is being drilled, the pulsed NMR means having:
      a) two tubular magnets, each having magnetic poles, and arranged so one pair of like magnetic poles face one another;
      b) an antenna mounted between the two tubular magnets, and in the recess of the exterior surface of the drilling means; and
      c) driving circuitry means for driving the antenna, which is mounted in the housing of the drilling means; and
   3) means for carrying borehole fluid through the drilling means, which is surrounded by the two tubular magnets and the antenna,
   wherein the borehole fluid provides an electromagnetic signal, and the pulsed NMR means comprises a gradient coil means for canceling the signal of the borehole fluid by applying a pulsed magnetic field which is stronger in the borehole fluid and weaker at a stationary point in the formation.

2. The apparatus of claim 1 wherein the gradient coil is mounted in the same recess as the antenna.

3. The apparatus of claim 2, the recess in which the antenna and gradient coil are mounted is filled with a nonconducting material.

4. The apparatus of claim 3, comprising a slotted shield in the recess and radially outside the antenna coil.

5. The apparatus of claim 4, the recess in which the antenna and the gradient coil are mounted is filled with a ferrite.

6. The apparatus of claim 2, comprising a slotted shield in the recess and radially outside the antenna coil.

7. The apparatus of claim 5, the electromagnetic signal having extensions of a resonance region, wherein the gradient coil is wound in the recess on two sides of the antenna and is mounted to cancel the electromagnetic signal in the vicinity of the extensions of the resonance region.

8. The apparatus of claim 6, the electromagnetic signal having extensions of a resonance region, wherein the gradient coil is wound in the recess on two sides of the antenna and is mounted to cancel the electromagnetic signal in the vicinity of the extensions of the resonance region.

9. A method comprising:
   using one portion of a tool to drill a borehole having a longitudinal axis in an earth formation, wherein the borehole contains fluid;
   using another portion of the same tool to make nuclear magnetic resonance (NMR) measurements while the borehole is being drilled by producing a rotationally symmetric magnetic field about the longitudinal axis with two tubular magnets, each having magnetic poles, and arranged so one pair of like magnetic poles face one another, and an antenna mounted between the two tubular magnets, and producing a stationary point of the magnetic field in the formation;
   carrying the borehole fluid through both portions of the tool with a barrel defining a channel and isolating the two tubular magnets from the borehole fluid; and
   canceling a resulting electromagnetic signal of the borehole fluid with a gradient coil which is coiled about the longitudinal axis.

10. The method of claim 9, using a pulsed current source to drive the gradient coil and cancel the borehole fluid electromagnetic signal by applying a pulsed magnetic field which is stronger in the borehole fluid and weaker at the stationary point.

11. The method of claim 10, using a gradient coil which is coiled longitudinally above and below the antenna to cancel the borehole fluid electromagnetic fluid.

12. The method of claim 11, producing the magnetic field through a slotted shield which is adjacent the antenna.

13. A method comprising:
    drilling a borehole in a formation with a drill assembly having a drill bit, a channel, and housing;
    making pulsed nuclear magnetic measurements of the formation with a pulsed NMR device in the housing while drilling the borehole, the NMR device comprising two tubular magnets, each having magnetic poles, and arranged so one pair of like magnetic poles face one another;
    driving an antenna mounted on the drilling means between the two tubular magnets;
    holding borehole fluid in the channel of the drilling assembly, wherein the channel is surrounded by the two tubular magnets and the antenna, such that the borehole fluid has an electromagnetic signal;
    pulsing a magnetic field into the formation with a gradient coil, wherein the magnetic field is stronger in the borehole fluid and weaker at a stationary point in the formation; and
    canceling the electromagnetic signal of the borehole fluid.

14. The method of claim 13, comprising:
    driving the gradient coil with a pulsed current source.

15. The method of claim 14, comprising:
    pumping drilling fluid through the channel of the drilling assembly.

16. The method of claim 15, comprising:
    producing a magnetic field through a slotted shield which is adjacent the antenna.

17. The method of claim 16, comprising:
    canceling the electromagnetic signal of the borehole fluid using a gradient coil which is coiled longitudinally above and below the antenna, relative to a longitudinal axis of the drill assembly.

18. The method of claim 17, the borehole electromagnetic signal having extensions of resonance regions, the steps comprising:

siting the gradient coil on the drilling assembly to cancel the borehole electromagnetic signal in the vicinity of the extensions of the resonance region.

19. The method of claim 15, comprising:

siting the gradient coil on the drilling assembly to cancel the borehole electromagnetic signal in the vicinity of the extensions of the resonance region.

20. A method for measuring the nuclear magnetic resonance of an earth formation surrounding a borehole containing a fluid while drilling the borehole, comprising the steps of:

(a) drilling the borehole into the earth formation with a logging-while-drilling nuclear magnetic resonance (LWD-NMR) tool;

(b) allowing the borehole fluid to circulate through the LWD-NMR tool;

(c) creating a static magnetic field in the earth formation and the borehole fluid with the LWD-NMR tool;

(d) transmitting an oscillating signal into the earth formation and borehole fluid to excite protons in the formation and borehole fluid with the LWD-NMR tool;

(e) producing a nuclear magnetic resonance signal from the earth formation and borehole fluid in response to the oscillating signal with the LWD-NMR tool;

(f) producing a borehole signal into the borehole fluid to reduce a resulting electromagnetic signal of the borehole fluid with the LWD-NMR tool; and (g) detecting a resulting signal indicating a nuclear magnetic measurement of the earth formation while drilling with the LWD-NMR tool.

21. The method of claim 20, wherein an antenna produces the borehole signal to reduce the electromagnetic signal of the borehole fluid.

22. The method of claim 21, using a pulsed current source to drive the antenna to apply a pulsed magnetic field which is strong in the borehole fluid and weak at a stationary point of the static magnetic field in the earth formation, thereby reducing the nuclear magnetic resonance signal of the borehole fluid.

23. The method of claim 22, producing the static magnetic field in the formation with at least one magnet.

24. The method of claim 23, producing the borehole signal through a slotted shield which is adjacent the antenna.

25. An apparatus for measuring the nuclear magnetic resonance of an earth formation surrounding a borehole containing a fluid while drilling the borehole, comprising:

(a) a means for drilling the borehole into the earth formation with a logging-while-drilling nuclear magnetic resonance (LWD-NMR) tool;

(b) a means for allowing the borehole fluid to circulate through the LWD-NMR tool:

(c) a means for creating a static magnetic field in the earth formation and the borehole with the LWD-NMR tool, (d) a means for transmitting an oscillating signal into the earth formation and borehole fluid to excite protons in the formation and borehole fluid with the LWD-NMR tool, (e) a means for producing a nuclear magnetic resonance signal from the earth formation and borehole fluid in response to the oscillating signal with the LWD-NMR tool; and (f) a means for producing a borehole signal into the borehole fluid to reduce a resulting electromagnetic signal of the borehole fluid with the LWD-NMR tool and detecting a resulting signal indicating a nuclear magnetic measurement of the earth formation while drilling with the LWD-NMR tool.

26. The apparatus of claim 25, the means for producing a borehole signal comprises a means for applying a pulsed magnetic field which is strong in the borehole fluid and weak at a stationary point of the static magnetic field in the earth formations to reduce the borehole fluid electromagnetic signal.

27. The apparatus of claim 25, wherein the means for producing comprises an antenna.

28. The apparatus of claim 27, the means for creating a static magnetic field comprises at least one magnet.

29. The apparatus of claim 28, comprising a tool housing a) b) c) and d), the tool having a surface which is adjacent the antenna and through which the borehole signal is produced.

30. An apparatus comprising:

1) a drilling means having:
   a) means for holding a drill bit for drilling a borehole in a formation; and
   b) an exterior surface, 2) a pulsed NMR means, housed within the means for hold a drill bit, for making nuclear magnetic resonance (NMR) measurements of the formation while the borehole is being drilled, the pulsed NMR means having:
   a) two portions of a static magnet, each having magnetic poles, and arranged so one pair of like magnetic poles face one another; and
   b) an antenna mounted adjacent the two portions of the static magnets, beneath the exterior surface of the means for holding a drill bit, 3) means for carrying borehole fluid through the means for holding a drill bit and past the static magnet and the antenna as the borehole is drilled, wherein the borehole fluid has an electromagnetic signal, and the pulsed NMR means comprises a means for producing a field and canceling the signal of the borehole fluid by applying a field which is strong in the borehole fluid and weak at a stationary point in the formation.

31. A method comprising:

using one portion of a tool to drill a borehole having a longitudinal axis in an earth formation, wherein the borehole contains fluid;

using another portion of the same tool to make nuclear magnetic resonance (NMR) measurements while the borehole is being drilled by producing a rotationally symmetric magnetic field about the longitudinal axis with a static magnet and an RF antenna mounted to produce a stationary point of a magnetic field in the formation;

carrying the borehole fluid through both portions of the tool; and canceling a resulting electromagnetic signal of the borehole fluid with a field-producing device which substantially encircles the longitudinal axis.

32. A method comprising:

drilling a borehole in a formation with a drill assembly having a drill bit and a channel;

making pulsed nuclear magnetic-measurements of the formation with a pulsed NMR device in the housing, the NMR device comprising two portions of a static magnet, each having magnetic poles, and arranged so one pair of like magnetic poles face one another;

driving an antenna mounted on the drilling means between portions of the two static magnets;

passing borehole fluid through the channel of the drilling assembly, past the static magnet and the antenna, such that the borehole fluid has an electromagnetic signal;

producing a magnetic field which is strong in the borehole fluid and weaker at a stationary point, into the formation with a field-producing device; and canceling the electromagnetic signal of the borehole fluid.

33. A method for measuring the nuclear magnetic resonance of an earth formation surrounding a borehole containing a fluid while drilling the borehole, comprising the steps of:

drilling the borehole into the earth formation with a logging-while-drilling nuclear magnetic resonance (LWD-NMR) tool;

providing a circulation path for borehole fluid through the LWD-NMR tool;

creating a static magnetic field in the earth formation with the LWD-NMR tool to align magnetic moments of protons in the formation in a first direction;

transmitting an oscillating signal from the LWD-NMR tool through a metallic portion of the tool and into the earth formation to sufficiently orient the magnetic moments of the protons in the formation to a second direction with the LWD-NMR tool to produce a detectable nuclear magnetic resonance signal in the earth formation in response to the oscillating signal; and detecting the detectable signal through the metallic portion to indicate a nuclear magnetic measurement of the earth formation while drilling with the LWD-NMR tool.

34. The method of claim 33, including transmitting the oscillating signal through a metallic shield on the LWD-NMR tool.

35. The method of claim 33, including transmitting a pulsed radio frequency signal through the metallic portion.

36. An apparatus for measuring the nuclear magnetic resonance of an earth formation surrounding a borehole containing a fluid while drilling the borehole, comprising:

a logging-while-drilling nuclear magnetic resonance (LWD-NMR) tool for drilling the borehole into the earth formation;

a path which allows borehole fluid to circulate through the LWD-NMR tool;

a magnetic device for creating a static magnetic field in the earth formation from the LWD-NMR tool to align in a first direction magnetic moments of protons in the formation;

a metallic shield on the LWD-NMR tool;

a transmitter for transmitting an oscillating signal through the metallic shield and into the earth formation to sufficiently orient the magnetic moments of the protons in the formation to a second direction with the LWD-NMR tool to produce a detectable nuclear magnetic resonance signal in the earth formation in response to the oscillating signal; and a receiver for detecting the detectable signal through the metallic shield to indicate a nuclear magnetic measurement of the earth formation while drilling with the LWD-NMR tool.

37. The apparatus of claim 36, wherein the metallic shield is configured to allow the transmission of the oscillating signal therethrough.

38. The apparatus of claim 36, wherein the oscillating signal is a pulsed radio frequency signal.

39. A method for measuring the nuclear magnetic resonance of an earth formation surrounding a borehole comprising the steps of:

creating a static magnetic field in the earth formation with a nuclear magnetic resonance NMR tool having a metallic housing;

aligning in a first direction magnetic moments of protons in the formation according to the static magnetic field;

transmitting an oscillating signal from the NMR tool through the metallic housing and into the earth formation;

sufficiently orienting in a second direction the magnetic moments of the protons in the formation with the oscillating signal to produce a detectable signal in the formation;

detecting the detectable signal through the metallic housing; and indicating a nuclear magnetic measurement of the earth formation with the NMR tool based on the detected signal.

40. The method of claim 39, including transmitting the oscillating signal through a slotted portion of the metallic housing of the NMR tool.

41. The method of claim 39, including transmitting a pulsed radio frequency signal through the metallic housing.

42. An apparatus for measuring the nuclear magnetic resonance of an earth formation surrounding a borehole comprising:

a means for creating a static magnetic field through a metallic housing and into the earth formation to align magnetic moments of protons in the formation in a first direction;

a transmitter for transmitting an oscillating signal through the metallic housing and into the earth formation to sufficiently orient magnetic moments of the protons in the formation to a second direction to produce a detectable signal in the formation; and a receiver for detecting the detectable signal through the metallic housing to indicate a nuclear magnetic measurement of the earth formation.

43. The apparatus of claim 42, wherein the metallic housing comprises a metallic portion which is configured to allow the transmission of the oscillating signal therethrough.

44. The apparatus of claim 42, wherein the oscillating signal comprises a pulsed radio frequency signal.

* * * * *